(12) United States Patent
McIntosh (10) Patent No.: US 10,691,200 B2
(45) Date of Patent: Jun. 23, 2020

(54) PERSONALIZED MULTI-SENSORY CUES AND PERSONALIZED SENSING IN A TARGETED ENVIRONMENT

(71) Applicant: THE BOEING COMPANY, Chicago, IL (US)

(72) Inventor: Darren Carl McIntosh, Mukilteo, WA (US)

(73) Assignee: The Boeing Company, Chicago, IL (US)

( * ) Notice: Subject to any disclaimer, the term of this patent is extended or adjusted under 35 U.S.C. 154(b) by 35 days.

(21) Appl. No.: 16/107,039

(22) Filed: Aug. 21, 2018

(65) Prior Publication Data

US 2020/0064905 A1 Feb. 27, 2020

(51) Int. Cl.
| | |
|---|---|
| *G06F 3/01* | (2006.01) |
| *A61B 5/1172* | (2016.01) |
| *A61B 5/1171* | (2016.01) |
| *G06K 9/00* | (2006.01) |
| *G06F 3/16* | (2006.01) |
| *A61M 21/00* | (2006.01) |
| *B60R 16/037* | (2006.01) |

(52) U.S. Cl.
CPC ............ *G06F 3/011* (2013.01); *A61B 5/1172* (2013.01); *A61B 5/1176* (2013.01); *A61M 21/00* (2013.01); *B60R 16/037* (2013.01); *G06F 3/017* (2013.01); *G06F 3/167* (2013.01); *G06K 9/00281* (2013.01); *G06K 9/00288* (2013.01); *G06K 9/00617* (2013.01); *A61M 2021/005* (2013.01); *A61M 2021/0016* (2013.01); *A61M 2021/0027* (2013.01); *G06F 2203/011* (2013.01)

(58) Field of Classification Search
CPC .......... G06F 3/017; G06F 3/011; G06F 3/167; G06F 2203/011; G06K 9/00288; G06K 9/00281; G06K 9/00617; B60R 16/037; A61M 21/00; A61M 2021/0016; A61M 2021/005; A61M 2021/0027; A61B 5/1172; A61B 5/1176
See application file for complete search history.

(56) References Cited

U.S. PATENT DOCUMENTS

| | | | |
|---|---|---|---|
| 2013/0068783 A1* | 3/2013 | Gasper | A01M 1/2038 222/1 |
| 2017/0337352 A1* | 11/2017 | Williams | G06F 21/32 |
| 2018/0014379 A1* | 1/2018 | Carvalho | H05B 37/0227 |

* cited by examiner

*Primary Examiner* — Muhammad N Edun
(74) *Attorney, Agent, or Firm* — Coats & Bennett, PLLC (57) ABSTRACT

Methods, systems and apparatuses are disclosed for delivering, in an enclosed environment, subject-directed multi-sensory stimuli output or sequence(s) to a specific subject based upon recognition and identification of a specific subject.

20 Claims, 9 Drawing Sheets

PERSONALIZED MULTI-SENSORY CUES AND PERSONALIZED SENSING IN A TARGETED ENVIRONMENT

TECHNOLOGICAL FIELD

The present disclosure relates generally to the field of characteristic recognition. More specifically, the present disclosure relates to the field of identity recognition for the purpose of delivering personalized sensory preferences to a population or sub-population.

BACKGROUND

The transportation industry has continued its attempts to improve the travel experience for passengers. Experience improvements have included increased comfort relative to passenger seats, leg room, cabin lighting and general cabin ambiance. Efforts to cater to customer needs relative to general convenience, including varied available beverage and food selections, have furthered the desired goals of improving customer service. Available media selections in the form of downloadable movies and other video programs, games and audio selections have further improved customer/traveler experiences on commercial transportation modes.

SUMMARY

According to an aspect of the present application, apparatuses, systems, and methods are disclosed for improving a traveler's experience in rooms and on vehicles, and other enclosed spaces including cabins and lavatories (e.g., lavatories and cabins in commercial vehicles including buses, trains RVs, ships and aircraft, etc.). Such systems include an improved passenger experience by including a plurality of subject-directed and otherwise targeted and preselected sensory stimuli delivered to a subject in response to at least one subject-specific identifying characteristic input. Present aspects further contemplate a plurality of subject-directed and otherwise targeted and preselected sensory stimuli delivered from a plurality of sensory stimuli outputs to a specific identified subject or class of subjects in response to and in concert with the presence and identification of the subject, preferably occurring in a contained area, environment and/or location.

Presently disclosed aspects further include apparatuses, systems, and methods for the collection and storage of identifying information of a specific subject, at least one detector and/or sensor for recognizing and identifying a specific subject, with the subject having at least one subject-specific identifying characteristic that is recognized by the system. If both a sensor and a detector are present in such systems, the sensor is in communication with the detector. The sensor and/or detector can send signals to a controller in communication with the sensor and/or detector. Aspects of the disclosed systems, apparatuses and methods further include a plurality of subject-directed sensory stimulus outputs in communication with the sensor, the detector and/or the controller. The plurality of subject-directed sensory stimulus outputs comprise at least two of: a subject-directed visual sensory stimulus output, a subject-directed olfactory sensory stimulus output and a subject-directed auditory sensory stimulus output. Each subject-directed sensory stimulus output is configured to emit at least one subject-directed and subject-specific sensory stimulus to a subject, with the subject-directed and subject-specific sensory stimulus including at least one of: a subject-directed visual sensory stimulus, a subject-directed olfactory sensory stimulus, and a subject-directed auditory sensory stimulus, with the subject-directed sensory stimulus outputs in communication with a controller. The plurality of the subject-directed sensory stimuli are directed to a predetermined location relative to and triggered by the presence of the specific subject in the predetermined location.

In another aspect, the detector comprises at least one of: a facial recognition detector, a fingerprint detector, a height detector, a weight detector, a card reader, an identification-chip reader, etc., and combinations thereof.

In a further aspect, the subject-directed sensory stimulus output includes and delivers one or more subject-specific or personalized sensory stimulus output including one or more of: a subject-directed visual sensory stimuli, a subject-directed olfactory stimuli, and a subject-directed auditory sensory stimuli.

A further aspect is directed to a method for delivering a plurality of sensory stimuli to a subject. The disclosed method includes inputting at least one subject-specific identifying characteristic input of a subject into a subject recognition system, with the subject recognition system in communication with at least one sensor or one detector. The method further includes sensing or detecting a subject-specific identifying characteristic input and sending a signal from the sensor or detector to a plurality of subject-directed sensory stimuli outputs. In further aspects, present methods include activating, including for a predetermined duration, at least one subject-directed sensory stimulus from each of the plurality of sensory stimuli outputs, with the subject-directed sensory stimuli including at least one of: a subject-directed visual sensory stimuli, a subject-directed olfactory sensory stimuli and a subject-directed auditory sensory stimuli The delivery of the plurality of the subject-directed sensory stimuli is controlled by at least one controller, with the controller in communication with the subject-directed sensory stimuli outputs, and delivering the plurality of the subject-directed sensory stimuli from the subject-directed sensory stimuli outputs to a predetermined location relative to and triggered by the presence of the recognized specific subject in a predetermined location.

The features, functions and advantages that have been discussed can be achieved independently in various aspects or may be combined in yet other aspects, further details of which can be seen with reference to the following description and the drawings.

BRIEF DESCRIPTION OF THE DRAWINGS

Having thus described variations of the disclosure in general terms, reference will now be made to the accompanying drawings, which are not necessarily drawn to scale, and wherein:

DETAILED DESCRIPTION

Aspects of the present application are directed to positively impacting a passenger experience by targeting the passenger's cognitive pathway through synaethesia, or the union of an individual's senses working together to achieve a desired result or impact. Synethesia is commonly defined as a perceptual phenomenon in which stimulation of one sensory or cognitive pathway leads to automatic, involuntary experiences in a second sensory or cognitive pathway. By providing a plurality of sensory stimuli to a passenger substantially simultaneously or in a programmed and predetermined sequence, the systems, apparatuses and methods disclosed herein promote a perception of cleanliness, freshness, spaciousness and even calm and restfulness via themed and/or sequenced sensory stimuli directed to an individual passenger's preferences. Providing such a sensory themed experience, especially in enclosed quarters sometimes considered less than spacious (e.g., aircraft and other lavatories, aircraft and other vehicle passenger cabins, etc.), results in an improved passenger experience that improves customer/passenger satisfaction.

Aspects of the present application are directed to apparatuses, systems, and methods for identifying individual subjects, tracking or otherwise determining a present position or location of such individual subjects, and then delivering or directing one or more of a plurality of preselected subject-specific and subject-directed sensory stimuli preferences to the subject for the purpose of delivering a personalized experience for a predetermined duration while the subject inhabits a predetermined location within a particular habitat that is preferably an enclosed space, including for example, a cabin or lavatory within, for example, a vehicle such as a passenger vehicle. The terms "subject-directed sensory stimulus" and "subject-directed sensory stimulus stimuli" as used herein refer to subject-specific stimuli that are then directed to a specific, recognized and identified individual subject, or class of subjects. The "subject-directed sensory stimulus" and "subject-directed sensory stimulus" can be equivalently referred to herein as "subject-specific sensory stimuli" and "subject-specific sensory stimulus".

According to present aspects, personalized, subject-specific preferences are collected, for example, by way of surveying an individual through answering a written survey, answering a verbally administered survey, etc. Preferences can also be gleaned (by subject permission, where regulations require such permission, etc.), for example, from social media sites to which the subject subscribes, or by employing a search engine to obtain background information on a subject (by permission of the subject, where such permission is first required), from other sites or sources that contain information relating to some or all of the surveyed inquiries, from collected biometrics, and by other means, etc.

Solicited subject-specific preferences can range broadly to include subject preferences concerning any number of biographical or other subject preferences across a widely varying range of topics including, for example and without limitation, recreational and professional interests, leisure and athletic activities, fashion preferences, musical preferences, preferences related to the arts, literature, movies, books, poems, magazines, authors, travel history, favorite destinations, personal history with respect to past, present or aspirational geographic locations as well as scenes relating to preferred geographic locales (e.g., mountains, prairies, deserts, cityscapes, oceans, seashores, jungles, etc.), alma mater-oriented educational institutions, favorite sports, professional and/or collegiate and/or high school sports teams, personalities, music, musical groups, and any other information able to attribute preferences and favorable experiences to a subject, including scents and colors, etc. Once the subject directly volunteers or otherwise provides such solicited topical background information, such preferences are stored into a retrievable system memory (e.g., a retrievable memory and file that can be accessed remotely and automatically, etc.) such as in a file that is specific to a particular subject.

Once subject-specific information has been collected, a subject-specific preference profile is generated or otherwise created or provided that takes into account the subject preferences and synthesizes a personalized and subject-specific set of subject-specific visual, olfactory and auditory preferences in the form of subject-specific sensory stimuli that are to be directed to a specific subject as subject-directed sensory stimuli. Once the subject-specific preferences are generated and, for example, stored into a subject-specific profile, the profile can be synthesized into a produced sequence or "suite" or collection of multi-sensory images, sounds, and scents that is personalized to a specific subject, and ready to be delivered to a specific subject at a predetermined location where subject-directed sensory outputs are located. To determine the location of a particular and specific subject within a population, aspects of the present systems, apparatuses and methods further identify, "track", or otherwise determine and confirm the location of the specific subject.

According to further aspects of the present application, apparatuses, systems, objects comprising the systems, and methods are disclosed for identifying the presence of a specific subject (e.g., an individual including, for example, a passenger, etc.) by detecting or sensing and recognizing a stored identifying characteristic of the subject (e.g., for the purpose of identifying the specific subject) and determining the location of the specific subject within an environment such as, for example, a predetermined and identifiable location within, for example, an enclosed environment. Once a specific subject is detected and identified (e.g., "recognized"), at least one of a plurality of preselected subject-specific preferences of the specific subject, in the form of subject-directed sensory stimuli are delivered to the specific subject via at least one of a plurality of subject-directed sensory stimuli outputs.

According to present aspects, identification and tracking systems are disclosed where a subject (e.g., an individual or person that can be, for example, a passenger, etc.) has identifying characteristics that are voluntarily or involuntarily collected or otherwise submitted to a system at a system information collection input. Identifying characteristics can be, without limitation, recognizable physical identifying characteristics specific to and otherwise associated with the subject, and include, for example, a facial feature, a retina scan, a corneal scan, a collection of facial features, vocal patterns or tones (e.g., sounds emanating from a voice, etc.), a fingerprint, further biometrics, etc. Such recognizable physical identifying characteristics further include more general identifying characteristics including, for example, weight, height, etc.

Identifying characteristics of a subject can further include any personal information that can be transferred onto or otherwise incorporated into any medium capable of storing such information and then having such stored information retrieved or "read", or otherwise deciphered. Such storable and readable information can, for example, be encoded on a readable identifying object carried on the person of the subject. For example, such a readable identifying object carried on the person of a subject can include, for example, a card, pin, bracelet, patch, chip, smart phone, other personal electronic device or personal electronic device application (equivalently referred to herein as an "app"), etc. that can be carried or worn by the subject. Such readable identifying objects contain information that can be encoded or otherwise incorporated into, for example, magnetic strips, bar codes, chips, RFID chips, or other information storage means, etc., that can be read or otherwise deciphered from the identifying object by a reader, scanner, detector, etc. Further readable identifying objects can include, small (e.g., nano-sized, etc.) chips, particles, etc., that can be inserted into a subject, and that contain subject-specific identifying information that can be read by a compatible detector.

Once a specific subject has been identified in a particular location having presently disclosed systems and apparatuses installed therein, and according to presently disclosed methods, subject-specific and subject-directed sensory stimuli outputs (SSOs) are activated for the purpose of delivering one or more of a plurality of subject-directed sensory stimuli from the subject-directed sensory stimuli outputs. The resulting presentation of subject-specific sensory stimuli preferences directed to a subject will result in, contribute to, or otherwise engender a pleasing experience to the subject, and serve to pleasurably surprise the subject receiving such a multi-sensory preferential production and sequence presentation for the duration of time such subject resides in or inhabits a particular location within an enclosed space, such as, for example, a passenger vehicle lavatory, etc. (e.g., an aircraft lavatory, etc.).

Figure 1A:
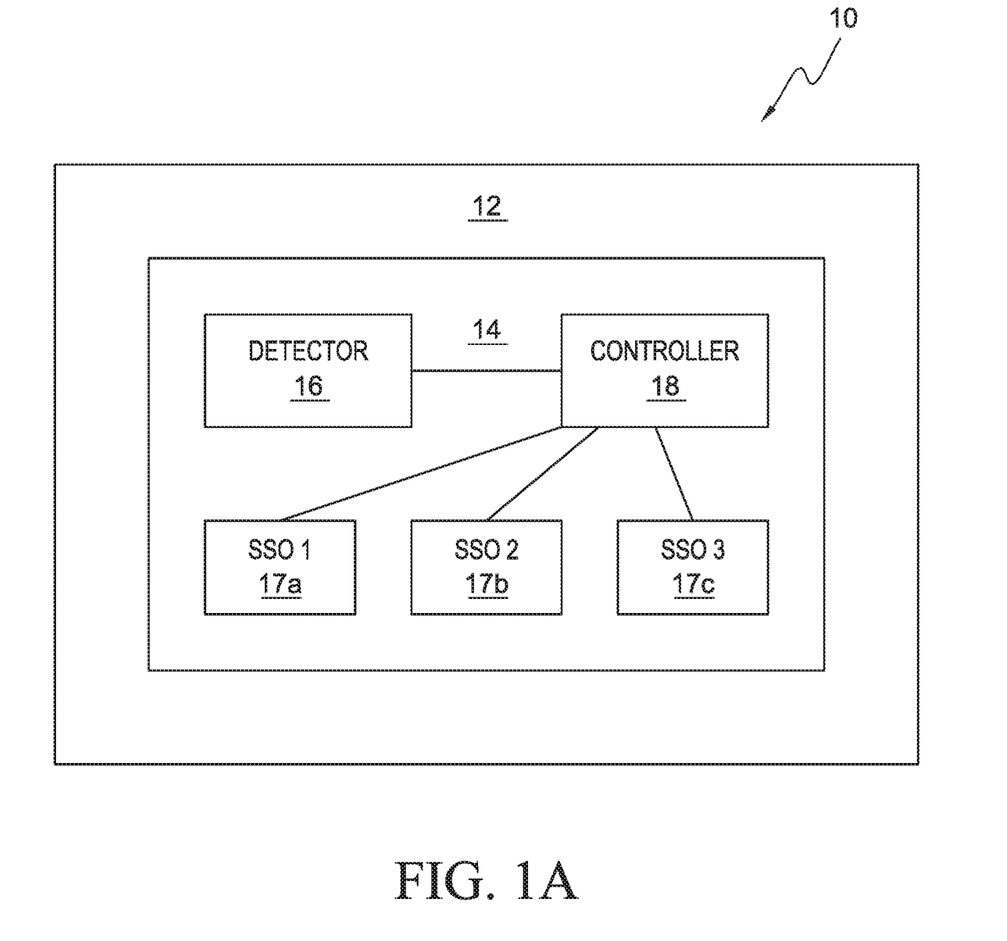
FIG. 1A is an illustration of a system according to aspects of the present disclosure.
Figure 1B:
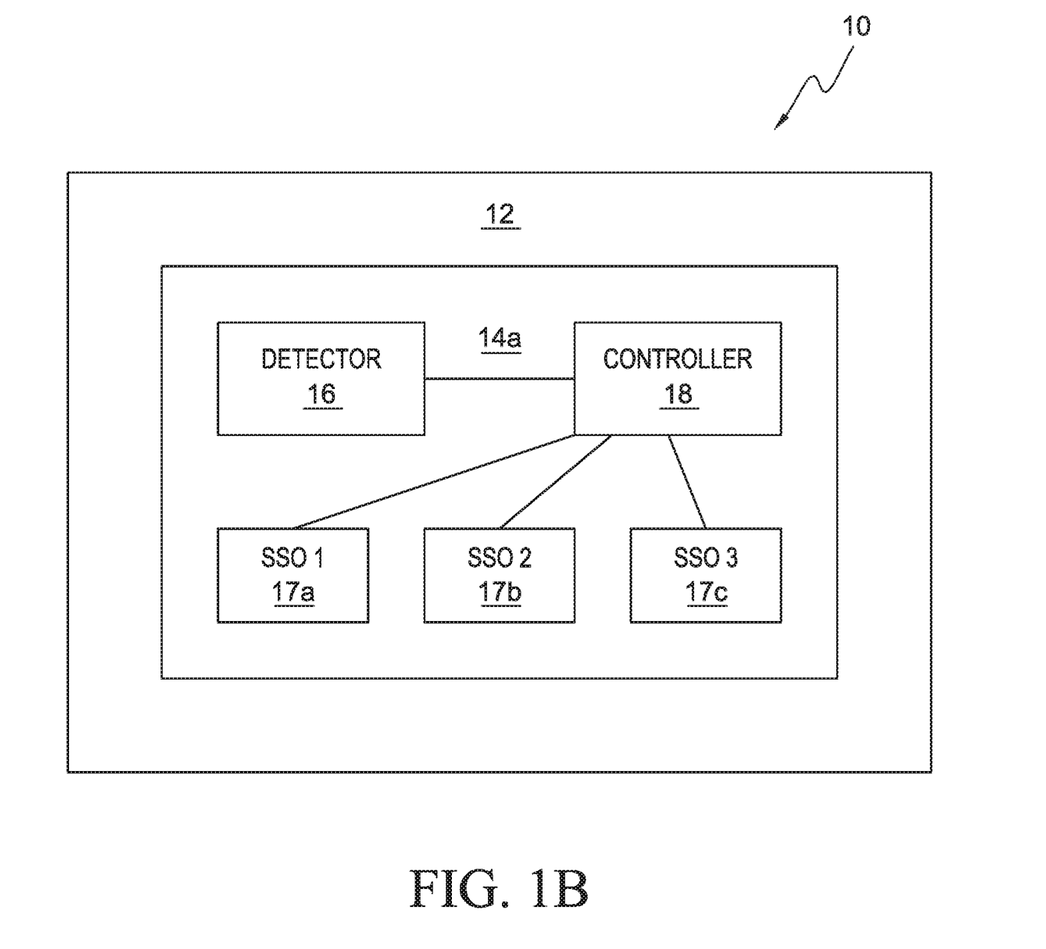
FIG. 1B is an illustration of an apparatus according to aspects of the present disclosure.

As shown in FIG. 1A, an object 10 such as, for example, a vehicle that can be an aircraft comprises an enclosed environment 12 or interior space that further comprises a subject-directed sensory stimuli system 14 (system 14 equivalently referred to herein as apparatus 14, when the feature of system 14 are included within the apparatus 14a; see FIG. 1B) according to aspects of the present disclosure. The subject-directed sensory stimuli system comprises a detector 16 in communication with a controller 18. The controller 18 is further in communication with a plurality of subject-directed sensory stimulus outputs (17a)(17b)(17c) shown as SSO 1, SSO 2 and SSO 3, respectively. As shown in FIG. 1A, each subject-directed sensory stimuli output can be directed to a different sensory application. That is, as shown in FIG. 1A, for example, subject-directed sensory stimulus output SSO 1 (17a) can be a subject-directed visual sensory stimulus output responsible for, for example, producing or otherwise displaying a visual output including a visual image and/or a lighting effect (e.g., a light of a particular color or colors preferred by the subject, etc.). Subject-directed visual sensory stimulus output (17a) can further include a video projection device, a hologram projection device, a lighting element, a virtual reality output, etc.

As shown in FIG. 1B, an object 10 such as, for example, a vehicle that can be an aircraft comprises an enclosed environment 12 or interior space that further comprises a subject-directed sensory stimuli apparatus 14a according to aspects of the present disclosure. The subject-directed sensory stimuli system comprises a detector 16 in communication with a controller 18. The controller 18 is further in communication with a plurality of subject-directed sensory stimulus outputs (17a)(17b)(17c) shown as SSO 1, SSO 2 and SSO 3, respectively. As shown in FIG. 1B, each subject-directed sensory stimuli output can be directed to a different sensory application. That is, as shown in FIG. 1B, for example, subject-directed sensory stimulus output SSO 1 (17a) can be a subject-directed visual sensory stimulus output responsible for, for example, producing or otherwise displaying a visual output including a visual image and/or a lighting effect (e.g., a light of a particular color or colors preferred by the subject, etc.). Subject-directed visual sensory stimulus output (17a) can further include a video projection device, a hologram projection device, a lighting element, a virtual reality output, etc.

As shown in FIGS. 1A and 1B, for example, subject-directed sensory stimulus output SSO 2 (17b) can be a subject-directed olfactory sensory stimulus output responsible for, for example, producing or otherwise emitting an olfactory-based scent or combination of complimentary scents that can programmed to emit scents in concert with or to otherwise complement the visual sequence of images being produced by the subject-directed visual sensory stimulus output (17a). Still further, according to certain aspects, and as shown in FIGS. 1A and 1B, for example, subject-directed sensory stimulus output SSO 3 (17c) can be a subject-directed auditory sensory stimulus output responsible for, for example, producing or otherwise emitting an auditory-based sound or assemblage of sounds including, for example, music or spoken text, etc., to complement the visual sequence of images being produced by the subject-directed visual sensory stimulus output (17a) alone or in combination with the scents emitted by the subject-directed olfactory sensory stimuli output (17b). In this way, the specific subject that is detected and identified (e.g., "recognized") by the disclosed systems unexpectedly and automatically experiences a tailored and personally produced multi-sensory experience of visual, auditory and olfactory stimuli delivered to the subject substantially simultaneously or in a predetermined sequence, for example, while the subject resides in an aircraft or other passenger vehicle compartment, cabin or lavatory, or elsewhere within a preferably enclosed environment. The subject-directed visual, olfactory and auditory sensory outputs can be integrated into a single unit, or can be present as discrete units that can be in communication with each other and/or that can be in communication with the detector 16 and/or the controller 18.

Figure 2:
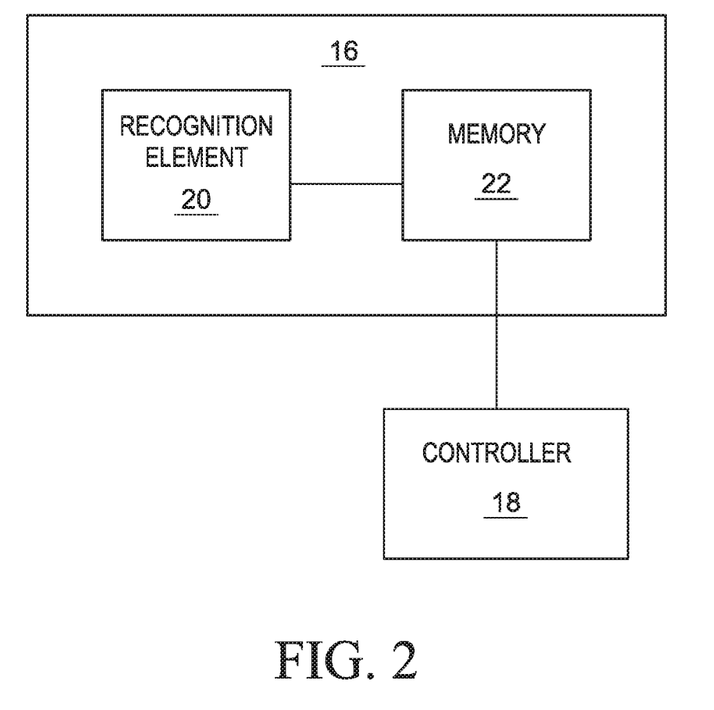
FIG. 2 is an illustration of the recognition system set forth in FIG. 1 and according to aspects of the present disclosure.

FIG. 2 shows a representative and exemplary illustration of a detector 16 that can be incorporated into the presently disclosed systems and apparatuses, such as those shown in FIGS. 1A and 1B. Detector 16 includes a recognition element 20 in communication with a memory 22 or other storage function. Recognition element 20 can be any device able to perceive a subject-specific identifying characteristic for the purpose of positively identifying and recognizing a subject. In a situation where, for example, an airline issues a card to a passenger with a magnetic chip or other element able to contain identifying subject-specific identifying, such card can contain readable information detected by the recognition element 20 (referred to equivalently herein as a "reader" or "information reader"). In further aspects, the recognition element can be a bar code reader that ascertains information printed, for example, on a boarding pass, or a bracelet issued to the subject/passenger. In such an instance, the recognition element 20 can, for example, read a passenger's seat number encoded into the bar code to identify the subject. In such an instance, the recognition element 20, for example, accesses the memory 22 for information on the particular passenger/subject occupying the particular seat, and a multi-sensory stimuli sequencing signal can be accessed from the memory 22 by the controller 18 to, for example, initiate a subject-specific and subject-directed multi-sensory stimuli production sequence for the enjoyment of the subject so identified.

Figure 3:
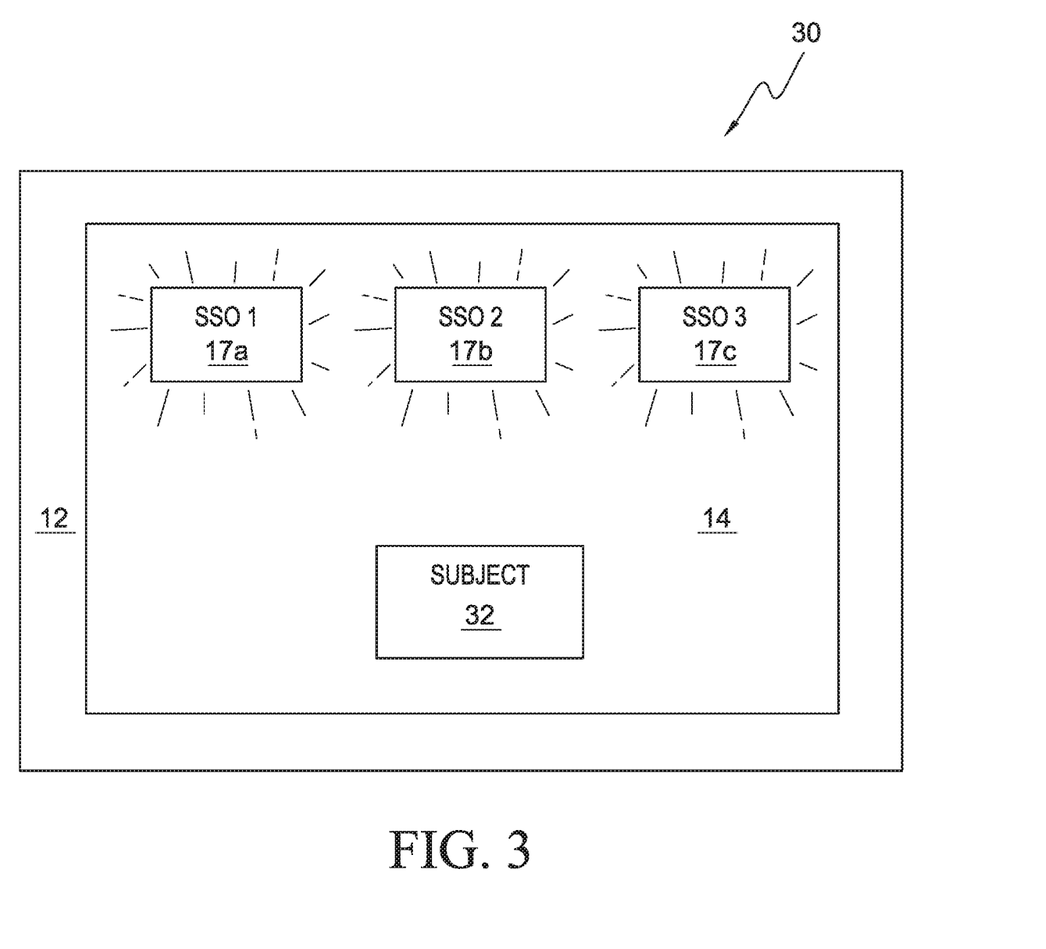
FIG. 3 is an illustration of a subject-directed sensory stimulus output system shown in FIG. 1, and according to aspects of the present disclosure.
Figure 4:
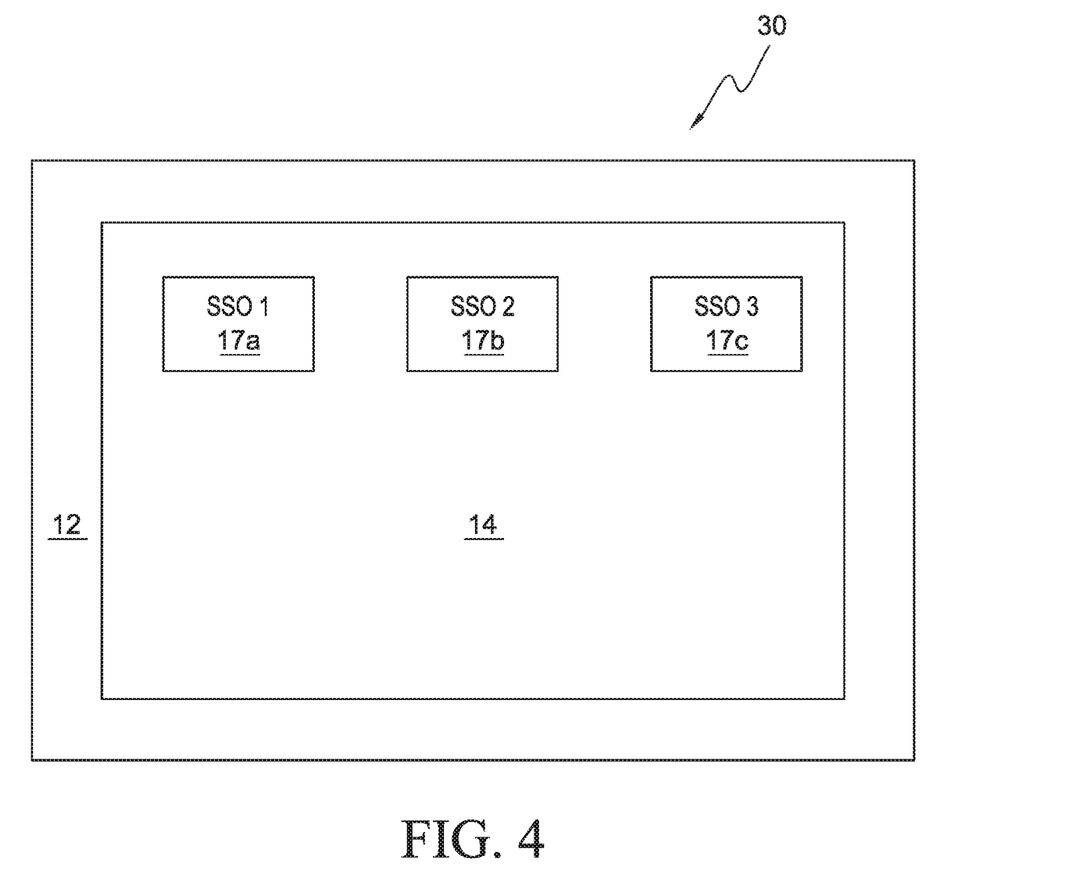
FIG. 4 is an illustration of a subject-directed sensory stimulus output system shown at least in FIG. 1A, 1B, 2 or 3, and according to aspects of the present disclosure

FIGS. 3 and 4 show further aspects of the system and apparatuses described in FIGS. 1A and/or 1B, and/or FIG. 2. As shown in FIG. 3 an object 30 such as, for example, a vehicle (e.g., an aircraft, etc.) comprises an enclosed environment 12 or interior space (e.g., a lavatory, etc.) as shown in FIGS. 1A and 1B, that further comprises a subject-directed sensory stimuli system 14 according to aspects of the present disclosure. The subject-directed sensory stimuli system comprises a detector 16 in communication with a controller 18. The controller 18 is further in communication with a plurality of subject-directed sensory stimulus outputs SSO 1, SSO 2, and SSO 3 shown as 17a, 17b, 17c, respectively. As shown in FIG. 3, the system 14 has detected the presence of a subject 32 in proximity to the system 14, and the detector 16 has accessed a program from a memory (shown in FIG. 2). The subject-specific file has been accessed by the memory and delivered to the controller 18 that then activates the plurality of subject-directed sensory stimulus outputs 17a, 17b, 17c. Subject-directed visual sensory stimuli shown as stimuli lines 17a' emanate from subject-directed visual sensory stimuli output 17a. Subject-directed olfactory sensory stimuli shown as stimuli lines 17b' emanate from subject-directed olfactory sensory stimuli output 17b. In addition, subject-directed auditory sensory stimuli shown as stimuli lines 17c' emanate from subject-directed auditory sensory stimuli output 17c.

When a subject is detected as having vacated a particular location comprising the systems and apparatuses disclosed herein, the departure of the subject will be detected by the system, or a timed sequence provided by the system will terminate (or the presence of a new subject will be detected by the system) and the subject-directed sensory stimuli outputs reset or otherwise cease producing the subject-directed and subject-specific multi-sensory stimuli. As shown in FIG. 4, no subject has been detected by detector 16. As a result, the system 14 has not been activated and no sensory stimuli are emanating from the subject-directed sensory stimuli outputs 17a, 17b, 17c, as evidenced by the absence of stimuli lines 17a', 17b' or 17c emanating from the outputs 17a, 17b, 17c, respectively.

FIGS. 5, 6, 7, and 8 are block diagrams illustrating methods according to presently disclosed aspects, such methods incorporating the systems and apparatuses as shown in FIGS. 1A, 1B, 2, 3, and 4. According to present aspects, and the method 50 as outlined in FIG. 5, as a subject approaches or otherwise enters a location of enclosed environment comprising the presently disclosed subject-directed sensory stimuli system (e.g., an aircraft lavatory, etc.), the detector acquires subject-specific identifying characteristics that enable the system to recognize and confirm the identity of the subject, and subject-specific identifying characteristics are inputted into the recognition system of the detector 52. The subject specific identifying characteristics are detected 54 and one or more of the sensory stimuli outputs are signaled by the controller 55. At least one of the sensory stimuli outputs are activated 56 and at least one subject-directed sensory stimulus is directed to the subject 58 via the subject-directed sensory stimuli output(s).

Figure 5:
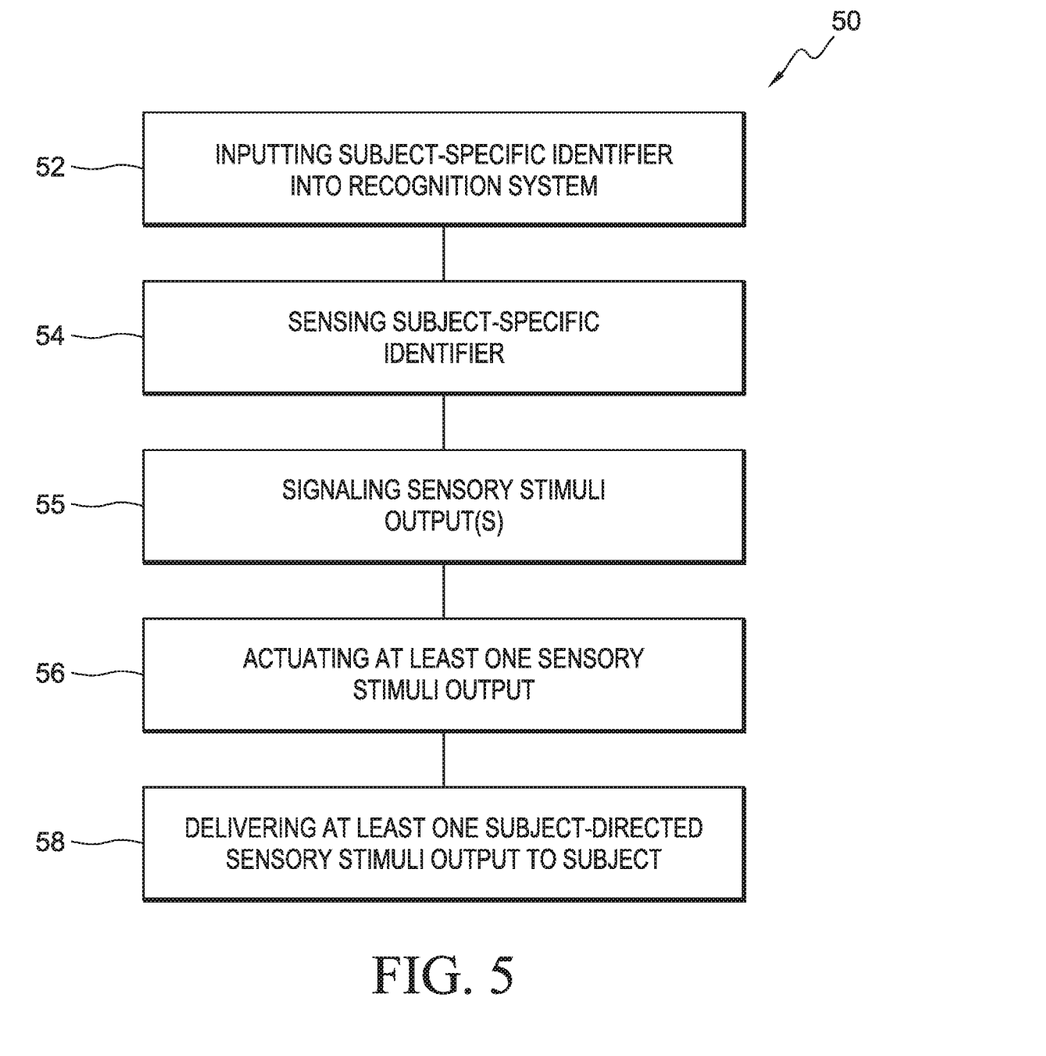
FIG. 5 is a flowchart illustrating a method according to an aspect of the present disclosure.
Figure 6:
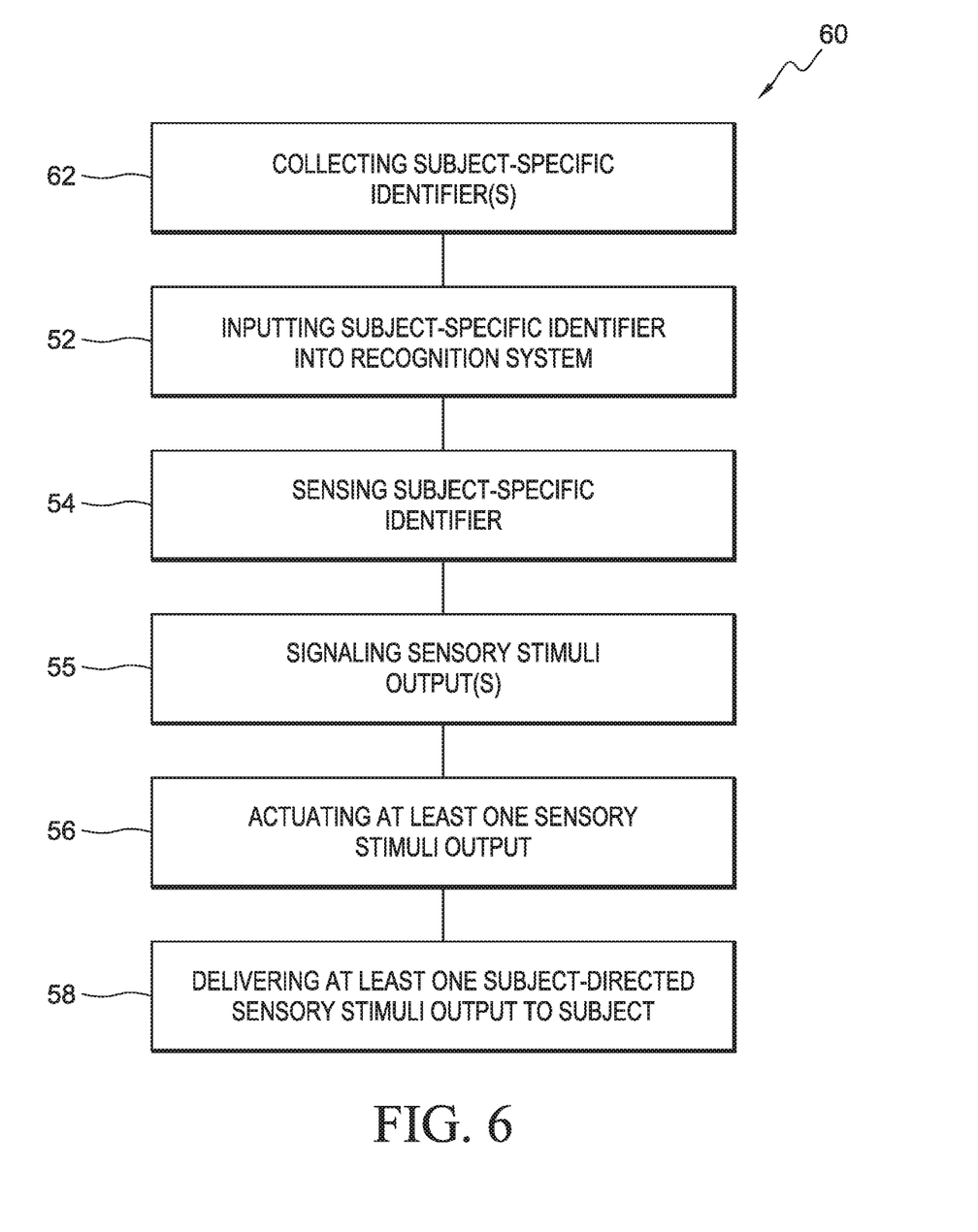
FIG. 6 is a flowchart illustrating a method according to an aspect of the present disclosure.

FIG. 6 shows a method 60 as illustrated in FIG. 5, with the additional preliminary step of first collecting 62 subject-specific preferences that are then either delivered to a retrievable subject-specific memory or are otherwise provided to the system.

Figure 7:
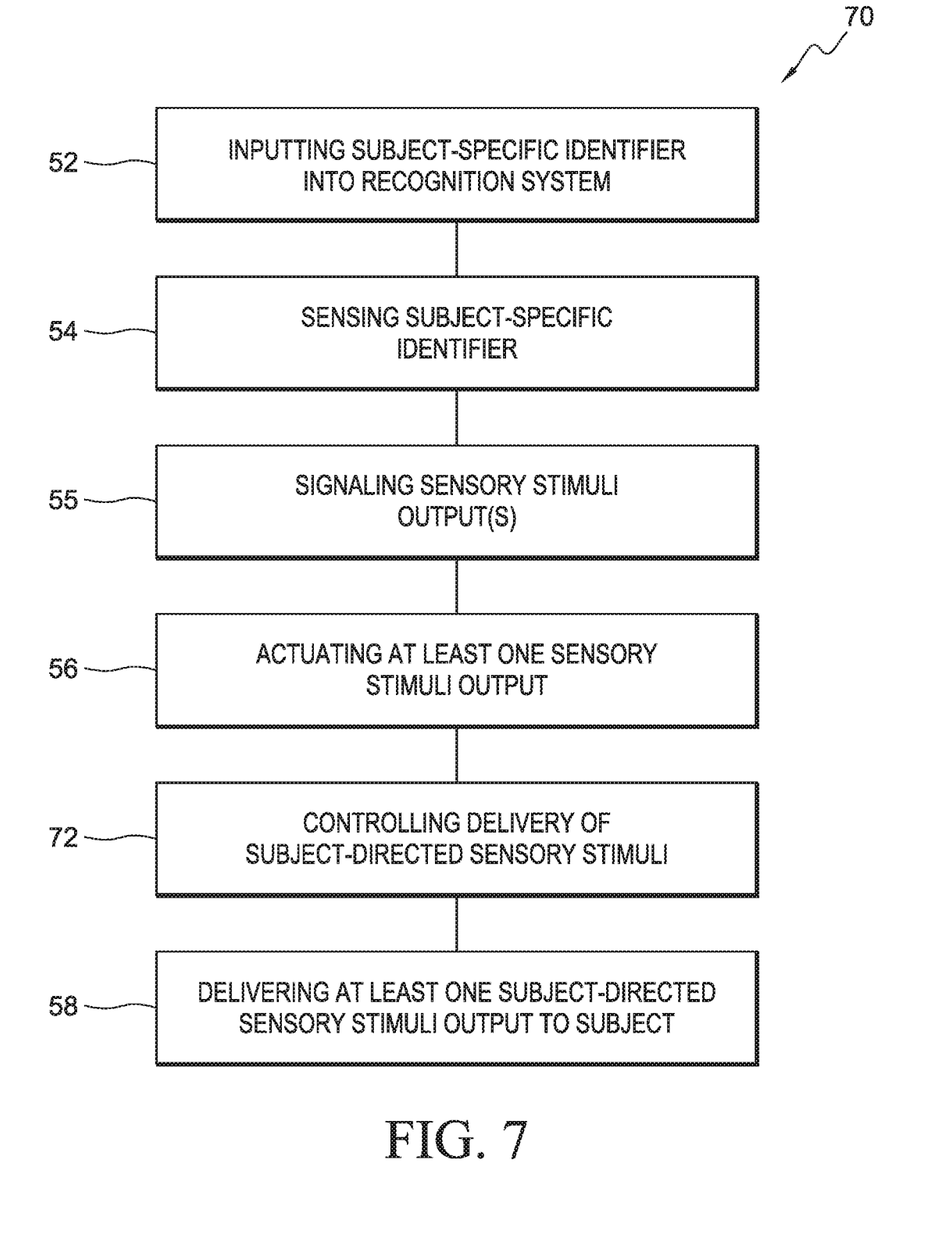
FIG. 7 is a flowchart illustrating a method according to an aspect of the present disclosure.

FIG. 7 shows the method 70 as illustrated in FIG. 5, with the additional steps of controlling 72 the delivery of the subject-directed sensory stimuli after activating 56 at least one subject-directed sensory stimuli output(s).

Figure 8:
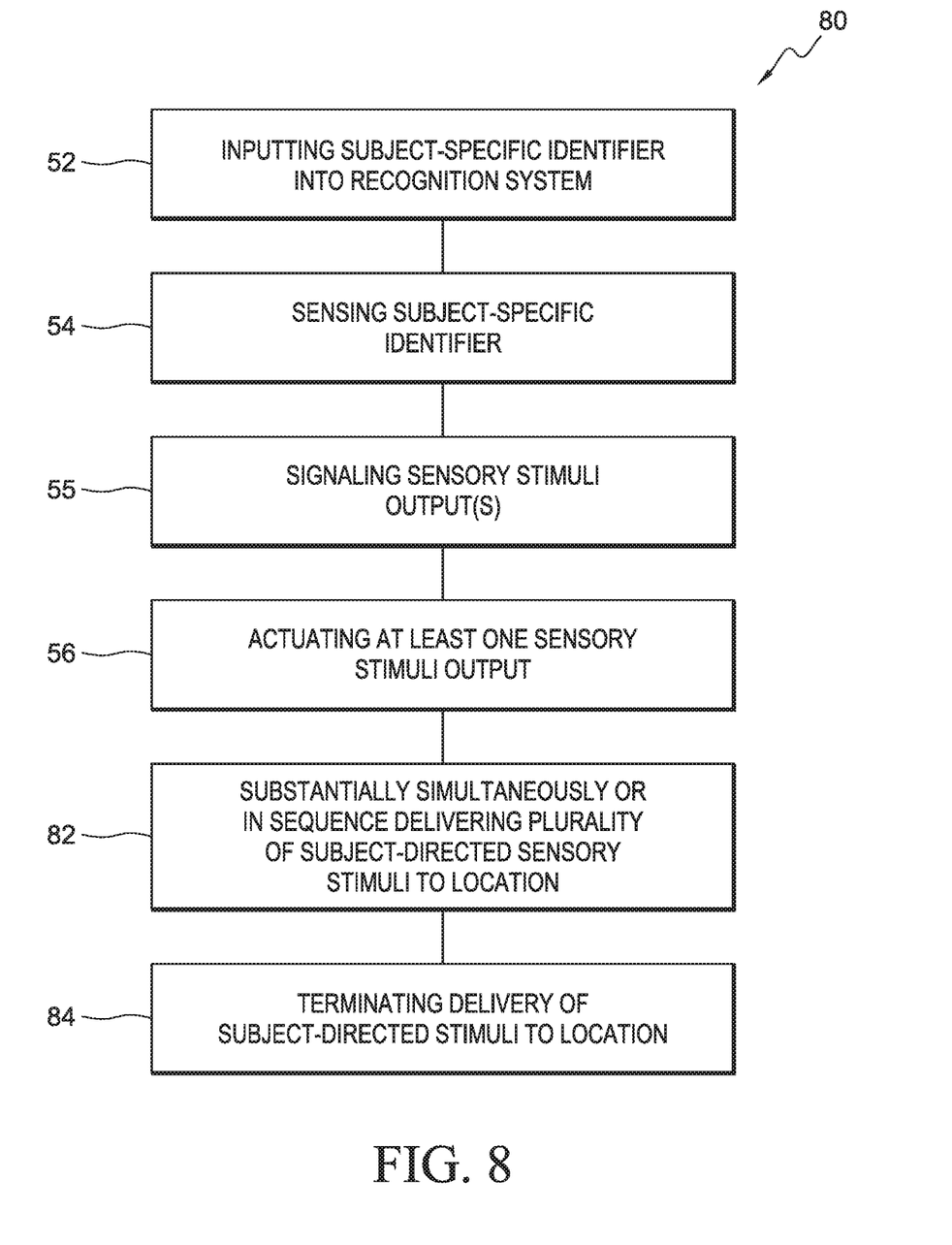
FIG. 8 is a flowchart illustrating a method according to an aspect of the present disclosure.

According to present aspects, in the method 80 as outlined in FIG. 8, as a subject approaches or otherwise enters a location of enclosed environment comprising the presently disclosed subject-directed sensory stimuli system (e.g., an aircraft lavatory, etc.), the detector acquires subject-specific identifying characteristics that enable the system to recognize and confirm the identity of the subject, and subject-specific identifying characteristics are inputted into the recognition system of the detector 52. The subject specific identifying characteristics are detected 54 and one or more of the sensory stimuli outputs are signaled by the controller 55. At least one of the sensory stimuli outputs are activated 56 and substantially simultaneously or in a predetermined and/or programmed sequence a plurality of subject-directed sensory stimuli are delivered 82 to a predetermined location inhabited by a specific subject. When the subject leaves the predetermined location positioned proximately to the subject-directed sensory stimuli system according to aspects herein, the delivery of the subject-directed sensory stimuli is terminated 84 or is otherwise reset to receive identifying information from a subsequent subject.

According to further aspects, a modular apparatus comprising the plurality of subject-directed sensory stimulus outputs in combination with the associated sensors, detectors, and controllers can be installed to deliver the plurality of sensory stimuli to a subject in response to at least one detected identifying characteristic of a subject. In other aspects, the disclosed systems are provided to a location that can be enclosed (e.g., a lavatory, First Class private suite or other private suite, cabin, room, change room, relaxation spa, sauna, etc.), with the systems incorporating a plurality of subject-directed sensory stimulus outputs in combination with the associated sensors, detectors, and controllers in varied locations and positions within an enclosed space or environment, but not necessarily within one modular unit.

The means for detecting and recognizing a subject, according to further aspects, can include recognition detectors and sensors used to detect, sense, or otherwise recognize identifying characteristics of a subject positioned at a location that is within range of such detectors and sensors. The detectors and sensors can detect subject identifying characteristics including facial features or a collection of facial features known collectively as facial recognition detectors. Further useful recognition detectors or sensors may further implement and analyze corneal or retinal scans (e.g., collectively referred to equivalently herein as "eye scans"). Still further, presently contemplated sensors or detectors can include fingerprint detectors, height and/or weight detectors, gesture recognition detectors, voice detectors, etc. for the purpose of recognizing and positively identifying an individual subject. In the case of height and/or weight detectors, and/or gesture recognition detectors, etc., present aspects further contemplate the recognition of a class of subjects such as, for example, children, whose weight and height would fall within or beneath a particular threshold (e.g., less than 4 feet in height or less than 70 pounds in weight, etc.). In these aspects, once a "class" of individuals (e.g., children) are detected and recognized, the present systems, apparatuses and methods can direct a themed sequence of multi-sensory stimuli that would generally "please" and "pleasantly surprise" a population or "class" of individuals.

Still further, presently contemplated recognition and identification apparatuses and systems include, card readers, chip readers, RFID readers, bar code readers, bar code scanners, etc. (collectively referred to herein as "information readers"). Such information readers can read encoded information from a medium that can be carried on, or may be otherwise attached to, a subject in the form of a card, bracelet, necklace, pin, patch, chip, smart phone, other personal electronic device or smart phone app or personal electronic device app, etc.

Aspects of the present disclosure contemplate not only identification of individual subjects, but also monitoring and determining the location of a particular subject. For example, during a flight, aspects of the present disclosure, contemplate various positioning or tracking systems employed as part of the subject-directed multi-sensory systems. Once a subject is detected within range of a particular location such as passenger seat, or a lavatory, the subject-directed sensory stimuli outputs can be engaged such that the subject receives the multi-sensory stimuli. Presently contemplated tracking, positioning, and identifying technologies such as Bluetooth, or other WiFi or modified wireless or GPS technology can be incorporated for these purposes into the presently disclosed systems, methods and apparatuses. Further tracking or positioning and identifying technologies include, but are in no way limited to, computer vision technology (e.g. computerized understanding and recognition from digital images or videos); deep learning (e.g. machine learning algorithms); sensor fusion (e.g. combinations of sensory data), etc. In these and other ways, present aspects contemplate the tracking and identification functions of the disclosed systems being able to follow the movement of a subject as the subject migrates through an environment and approaches, departs from, or resides within an enclosed area where the subject-directed multi-sensory stimuli outputs are located.

The subject-directed visual sensory stimuli outputs incorporated into presently disclosed systems and apparatuses include those able to respond to and otherwise receive signals from associated sensors, detectors, etc., and/or that can be controlled and actuated by associated controllers to deliver preselected and tailored visual images to a specific subject. The visual sensory stimuli outputs can include subject-directed visual images including, for example, video screens, hologram projectors, lighting elements, virtual displays, virtual reality displays, etc. for the purpose of automatically delivering scenes, movies, images, videos, lighting colors and/or lighting effects, etc. that coincide with the a subject's preferences, with such visual displays delivered to the subject in response to the subject's location and in response to the system's recognition of the subject's identifying characteristics. The visual images can further resemble a virtual window, panel, porthole, skylight, doorway, etc. for the purpose of appearing to enlarge an otherwise confined or enclosed space. As mentioned previously, the visual images or sequence of images can be delivered to a specific subject and in accordance with a specific subject's known preferences in concert with auditory stimuli and/or olfactory stimuli released from the presently disclosed systems.

The subject-directed auditory stimuli can be delivered to a recognized and identified subject according to the subject's known preferences independent of the visual and olfactory stimuli, or in concert with the visual and olfactory stimuli (e.g., for the purpose of complementing the visual and/or olfactory stimuli, etc.) presented to the specific identified subject. Such auditory stimuli can be delivered by, for example, sound speakers that are integrated into the disclosed systems, or that exists separate from the disclosed systems, but are desirably accessed by the disclosed multi-sensory systems. That is, aspects of the present disclosure contemplate accessing existing speakers that may occur at locations within an enclosed environment within a vehicle or other object (e.g., a building, etc.). When the subject-directed auditory stimuli is delivered to a specific subject, (e.g., from a subject-directed auditory sensory stimuli output such as from a sound-emitting device, etc.) such auditory stimuli can be sounds or an assemblage of sounds that, for example mimic or reproduce sounds found in nature (e.g., the wind blowing through fields or trees, ocean waves, birds chirping, etc.), as well as music, etc. The subject-directed auditory stimuli can be delivered to a specific subject in concert with or independent from the subject-directed visual stimuli. That is, for example, if a movie or music video or concert video sequence is being delivered to a subject via the visual sensory stimuli output, the auditory stimuli delivered to the subject from the auditory sensory stimuli output can be the soundtrack associated with the movie, or the music track associated with the music video or concert video.

The subject-directed olfactory sensory stimuli released to a recognized and identified subject via the subject-directed olfactory sensory stimuli output(s) according to a subject's known and recorded preferences can similarly be delivered to a subject independent of or in concert with simultaneously delivered subject-directed visual stimuli and subject-directed auditory stimuli. Such release of subject-directed olfactory stimuli to a specific subject (and according to a subject's known preferences), for example, from a scent-emitting device, etc., enables the subject to smell, and potentially even taste, a particular olfactory stimulus. For example, if the disclosed systems detect and identify a subject as a child, based on the known subject preferences, the systems of the present disclosure may present a multi-sensory sequence of a carnival or circus appearing outside (via the visual sensory output) of the enclosed space (e.g., aircraft lavatory) through a virtual window, complete with noise and music reminiscent of a circus or carnival (via the auditory stimuli output), along with the smell of popcorn, cotton candy, etc., (via the olfactory sensory output). The scents can be delivered from the presently disclosed systems via the subject-directed olfactory sensory stimuli outputs in dry, liquid, or aerosol form. Such scent delivery means can include cartridge-based, carousel-based, or individual scented packet or strip delivery to such device that can further include a means for producing a directed airflow such as, for example, an integrated fan or an air-jet, etc., that can be powered, for example, by a piezoelectric or other low current motor, etc.

When the presently disclosed systems are in communication with, or otherwise access, the internet (e.g., via available WiFi, etc.), a virtually limitless number of visual and auditory stimuli can be accessed and delivered via the respective visual and auditory outputs for the enjoyment and sensory consumption of an identified and recognized subject, all in accordance with a subject's personalized and known preferences. Examples of sensory combinations presented herein can be harmonized to complement one another, and are meant to be illustrative and are in no way limiting.

By way of a non-limiting example, subject-specific preferences for a particular subject may indicate a subject having nautical interests. According to present aspects, once such a subject is recognized, for example at or within an aircraft lavatory, the disclosed systems recognize and detect a specific subject, the subject's preferences are accessed by the system, and the system selects and delivers a subject-directed visual sensory stimulus output of seashores, oceans, beaches, etc., to a viewable location within the lavatory (e.g. a virtual window, porthole, mirror, wall panel, floor, ceiling, etc.) Substantially simultaneously, or in a desired sequence, the disclosed systems select and deliver a subject-directed auditory sensory subject output of nautical sounds including, for example, waves, seagulls, beach music, etc. in concert with or to otherwise complement and harmonize the auditory stimuli with the nautical visual effect presented to the subject by the visual stimuli output. Further, substantially simultaneously, or in a desired sequence, the disclosed systems select and deliver a subject-directed olfactory sensory subject output of nautical smells including, for example sea salt, suntan lotion, etc. in concert with or to otherwise complement and harmonize olfactory stimuli with the nautical visual and auditory effects presented to the subject by the visual and auditory stimuli outputs.

Further examples of the subject-directed sensory stimuli outputs that can be produced and delivered to a specific subject include, without limitation, any calming or desired scene to foster an overall subject-directed experience of freshness, cleanliness, etc. while also serving to expand the apparent dimension of an enclosed space. Such multi-sensory stimuli productions or sequences can, for example include, forest, space, fields, citrus groves, farms, cityscapes, etc., with complementary sounds and smells from respective auditory and olfactory sensory stimuli outputs accompanying the visual sensory stimuli, etc. If desired, the olfactory sensory stimuli output can deliver perfumes, colognes or other subject-directed scent preferences.

The presently disclosed systems also have particular utility for a population of individuals (subjects) that remain within an enclosed space, and (e.g., if desired, for a particular timed duration) where a preferential multi-sensory display would be beneficial, would surprise, and would be pleasing to a subject. Such environments include, for example, rooms and lavatories in hotels and other buildings as well as First Class private suites and other private and non-private suites, cabins, compartments, lavatories, change rooms, relaxation spas, saunas, etc., for example on vehicles, including passenger vehicles such as aircraft, rotorcraft, spacecraft, terrestrial vehicles including trains, buses, RVs, automobiles, and surface and sub-surface marine (e.g., waterborne) craft, hovercraft, satellites, etc.

For clarity in understanding the disclosure below, to the extent that "one of" a conjunctive list of items (e.g., "one of A and B") is discussed, the present disclosure refers to one (but not both) of the items in the list (e.g., an A or a B, but not both A and B). Such a phrase does not refer to one of each of the list items (e.g., one A and one B), nor does such a phrase refer to only one of a single item in the list (e.g., only one A, or only one B). Similarly, to the extent that "at least one of" a conjunctive list of items is discussed (and similarly for "one or more of" such a list), the present disclosure refers to any item in the list or any combination of the items in the list (e.g., an A only, a B only, or both an A and a B). Such a phrase does not refer to at least one of each of the items in the list (e.g., at least one of A and at least one of B).

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. A system comprising:
    a detector for recognizing a subject, the subject having at least one subject-specific identifying characteristic;
    a controller in communication with the detector;
    a plurality of differing subject-directed sensory stimulus outputs in communication with the controller, said subject-directed sensory stimulus outputs configured to emit at least two subject-directed sensory stimulus types to the subject, said subject-directed sensory stimulus types selected from the group consisting of: a subject-directed visual sensory stimulus, a subject-directed olfactory sensory stimulus, and a subject-directed auditory sensory stimulus;
    wherein the at least two subject-directed sensory stimulus types are directed to a predetermined location in response to the subject-specific identifying characteristic; and
    wherein at least two of the subject-directed sensory stimulus types are directed to a predetermined location in response to the subject inhabiting the predetermined location, said subject having the subject-specific identifying characteristic;
    wherein the subject-directed sensory stimulus types are predetermined sensory stimuli requested by a subject;
    wherein the subject-directed sensory stimulus types are delivered by the system in response to a pre-collected personalized and subject-specific set of subject-specific visual, olfactory and auditory preferences; and
    wherein the predetermined location is a location within a vehicle cabin.

2. The system of claim 1, wherein the detector comprises at least one of: a facial recognition detector, a voice detector, a gesture recognition detector, a fingerprint detector, a height detector, a weight detector, a card reader, an identification-chip reader, and RFID reader, a bar code scanner, a smart phone, a smart phone application, and combinations thereof.

3. The system of claim 1, wherein the subject-specific identifying characteristic comprises at least one of: a facial feature, a collection of facial features, a fingerprint, height, weight, encoded information on a card, encoded information on a chip, a corneal scan, a retinal scan, a gesture, and combinations thereof.

4. The system of claim 1, wherein the subject-directed sensory stimulus output comprises a subject-directed visual sensory stimuli output, said subject-directed visual sensory stimuli output comprising at least one of: a video screen, a hologram projector, a lighting element, and a virtual reality display.

5. The system of claim 4, wherein the subject-directed visual sensory stimulus comprises at least one of: a subject-directed visual image and a subject-directed lighting effect.

6. The system of claim 1, wherein the subject-directed sensory stimulus output comprises a subject-directed olfactory stimulus output, said subject-directed olfactory stimulus output comprising a scent-emitting device.

7. The system of claim 6, wherein the subject-directed olfactory sensory stimulus comprises a subject-directed scent.

8. The system of claim 1, wherein the subject-directed sensory stimulus output comprises a subject-directed auditory stimulus output, said subject-directed auditory stimulus output comprising a sound-emitting device.

9. The system of claim 8, wherein the subject-directed auditory sensory stimulus output emits a subject-directed sound or a subject-directed assemblage of sounds.

10. The system of claim 1, wherein the plurality of the subject-directed sensory stimuli is directed substantially simultaneously to the predetermined location.

11. The system of claim 1, wherein the predetermined location is a lavatory, wherein said lavatory is located within a vehicle cabin.

12. The system of claim 1, wherein the predetermined location is a vehicle passenger cabin.

13. An object comprising:
a system for delivering a plurality of differing sensory stimuli types to a subject in response to at least one identifying characteristic of the subject and in response to a location of the subject, the system comprising:
a detector for recognizing a subject, the subject having at least one subject-specific identifying characteristic;
a controller in communication with the detector;
a plurality of differing subject-directed sensory stimulus outputs in communication with the controller, said subject-directed sensory stimulus outputs configured to emit at least two subject-directed sensory stimulus types to the subject, said subject-directed sensory stimulus types selected from the group consisting of: a subject-directed visual sensory stimulus, a subject-directed olfactory sensory stimulus, and a subject-directed auditory sensory stimulus;
wherein at least one subject-directed sensory stimulus is directed to a predetermined location in response to the subject-specific identifying characteristic;
wherein at least two of the subject-directed sensory stimulus types are directed to a predetermined location in response to the subject located at the predetermined location, said subject having the subject-specific identifying characteristic;
wherein the subject-directed sensory stimulus types are predetermined sensory stimuli requested by a subject;
wherein the subject-directed sensory stimulus types are delivered by the system in response to a pre-collected personalized and subject-specific set of subject-specific visual, olfactory and auditory preferences; and
wherein the predetermined location is a location within a vehicle cabin.

14. The object of claim 13, wherein the vehicle cabin is located in a vehicle, said vehicle selected from the group consisting of: an aircraft, a spacecraft, a rotorcraft, a satellite, a terrestrial vehicle, a surface waterborne vehicle, a sub-surface waterborne vehicle, a hovercraft, and combinations thereof.

15. A method for delivering a plurality of subject-specific sensory stimuli to a subject, the method comprising:
inputting at least one subject-specific identifying characteristic of a subject into a recognition system, said recognition system in communication with at least one sensor;
detecting an identifying input via at least one detector, said identifying input specific to a subject;
sending a signal from the detector to at least two of a plurality of subject-directed sensory stimulus output types;
activating for a predetermined duration at least two of said plurality of subject-directed sensory stimulus output types, said plurality of subject-directed sensory stimulus output types comprising at least two of: a subject-directed visual sensory stimulus output, a subject-directed olfactory sensory stimulus output, and a subject-directed auditory sensory stimulus output;
delivering at least two of a plurality of a subject-directed sensory stimuli from at least two of the plurality of subject-directed sensory stimulus output types to a predetermined location, said predetermined location inhabited by the subject;
wherein the subject-directed sensory stimulus types are predetermined sensory stimuli requested by a subject;
wherein the subject-directed sensory stimulus types are delivered by the system in response to a pre-collected personalized and pre-collected subject-specific set of subject-specific visual, olfactory and auditory preferences; and
wherein the predetermined location is a location within a vehicle cabin.

16. The method of claim 15, wherein, before the step of inputting at least one subject-directed identifying characteristic of the subject into a recognition system, the method further comprising:
collecting identifying information specific to the subject.

17. The method of claim 15, in the step of delivering the at least two of the plurality of the subject-directed sensory stimuli, further comprising:
substantially simultaneously delivering the plurality of the subject-directed
sensory stimuli to the location inhabited by the subject.

18. The method of claim 15, wherein the predetermined location is a lavatory, wherein said lavatory is located within the vehicle cabin.

19. The method of claim 15, the step of detecting the identifying characteristic further comprising:
identifying the location of the subject within the vehicle cabin.

20. The method of claim 15, wherein the vehicle cabin is located in a vehicle, said vehicle selected from the group consisting of: an aircraft, a spacecraft, a rotorcraft, a satellite, a terrestrial vehicle, a surface waterborne vehicle, a sub-surface waterborne vehicle, a hovercraft, and combinations thereof.

* * * * *